United States Patent
Harper et al.

(10) Patent No.: US 8,556,929 B2
(45) Date of Patent: Oct. 15, 2013

(54) SURGICAL FORCEPS CAPABLE OF ADJUSTING SEAL PLATE WIDTH BASED ON VESSEL SIZE

(75) Inventors: Jennifer S. Harper, Westminster, CO (US); J. Bruce Dunne, Longmont, CO (US)

(73) Assignee: Covidien LP, Mansfield, MA (US)

( * ) Notice: Subject to any disclaimer, the term of this patent is extended or adjusted under 35 U.S.C. 154(b) by 508 days.

(21) Appl. No.: 12/696,592

(22) Filed: Jan. 29, 2010

(65) Prior Publication Data
US 2011/0190653 A1    Aug. 4, 2011

(51) Int. Cl.
- *A61B 17/28* (2006.01)
- *A61B 17/08* (2006.01)
- *A61B 5/04* (2006.01)
- *A61B 5/053* (2006.01)
- *A61B 5/103* (2006.01)

(52) U.S. Cl.
USPC .............. 606/207; 606/51; 606/52; 606/213; 600/202; 600/372; 600/547; 600/587

(58) Field of Classification Search
USPC ......... 73/1.08, 1.15, 760, 763, 781, 788, 789, 73/796; 600/104, 202, 218, 306, 372, 382, 600/546–548, 550, 554, 561–562, 587; 606/1, 27–29, 31–32, 34, 40, 48, 606/51–52, 148, 205, 210, 213, 207
See application file for complete search history.

(56) References Cited

U.S. PATENT DOCUMENTS

| | | | |
|---|---|---|---|
| 4,128,099 A | | 12/1978 | Bauer |
| 5,618,294 A | * | 4/1997 | Aust et al. ................. 606/170 |
| 5,693,051 A | * | 12/1997 | Schulze et al. ............. 606/51 |
| 5,791,231 A | * | 8/1998 | Cohn et al. ................. 92/88 |
| 5,810,881 A | * | 9/1998 | Hoskin et al. ............. 606/207 |
| 5,876,401 A | * | 3/1999 | Schulze et al. ............. 606/51 |
| 6,083,223 A | * | 7/2000 | Baker ...................... 606/52 |
| 6,096,037 A | * | 8/2000 | Mulier et al. .............. 606/49 |
| 6,126,665 A | | 10/2000 | Yoon |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

European Search Report for European Application No. 11152220 dated May 19, 2011.

(Continued)

*Primary Examiner* — Rene Towa
*Assistant Examiner* — Emily Lloyd

(57) ABSTRACT

A surgical forceps includes a housing having a shaft attached thereto and an end effector assembly disposed at a distal end of the shaft. The end effector assembly includes first and second jaw members having opposed seal plates, each of the seal plates having a width. At least one of the jaw members is moveable from an open position to a closed position for grasping tissue therebetween. A sensing component is configured to determine an output relating to a diameter of tissue or a composition of tissue disposed between the opposed seal plates of the first and second jaw members. An expanding component is configured to expand the width of at least one of the opposed seal plates according to the determined output.

11 Claims, 7 Drawing Sheets

(56) References Cited

U.S. PATENT DOCUMENTS

| | | | |
|---|---|---|---|
| 6,440,130 B1* | 8/2002 | Mulier et al. | 606/49 |
| 6,569,105 B1 | 5/2003 | Kortenbach et al. | |
| 6,610,060 B2* | 8/2003 | Mulier et al. | 606/49 |
| 6,613,048 B2* | 9/2003 | Mulier et al. | 606/49 |
| 6,656,175 B2 | 12/2003 | Francischelli et al. | |
| 6,755,338 B2* | 6/2004 | Hahnen et al. | 227/175.1 |
| 6,755,824 B2* | 6/2004 | Jain et al. | 606/41 |
| 6,858,028 B2* | 2/2005 | Mulier et al. | 606/51 |
| 7,001,408 B2* | 2/2006 | Knodel et al. | 606/207 |
| 7,025,763 B2* | 4/2006 | Karasawa et al. | 606/28 |
| 7,083,619 B2 | 8/2006 | Truckai et al. | |
| 7,108,694 B2* | 9/2006 | Miura et al. | 606/31 |
| 7,115,139 B2* | 10/2006 | McClurken et al. | 607/96 |
| 7,270,664 B2 | 9/2007 | Johnson et al. | |
| 7,491,201 B2 | 2/2009 | Shields et al. | |
| 2003/0078578 A1 | 4/2003 | Truckai et al. | |
| 2003/0236518 A1 | 12/2003 | Marchitto et al. | |
| 2004/0068274 A1 | 4/2004 | Hooven | |
| 2004/0143263 A1 | 7/2004 | Schechter | |
| 2005/0107824 A1* | 5/2005 | Hillstead et al. | 606/205 |
| 2005/0113826 A1 | 5/2005 | Johnson | |
| 2005/0171535 A1 | 8/2005 | Truckai | |
| 2008/0009860 A1 | 1/2008 | Odom | |
| 2008/0045947 A1 | 2/2008 | Johnson et al. | |
| 2008/0167644 A1* | 7/2008 | Shelton et al. | 606/34 |
| 2008/0195093 A1 | 8/2008 | Couture et al. | |
| 2008/0249527 A1 | 10/2008 | Couture | |
| 2008/0300580 A1* | 12/2008 | Shelton et al. | 606/1 |
| 2009/0012556 A1* | 1/2009 | Boudreaux et al. | 606/206 |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 19738457 | 1/2009 |
| EP | 1159926 | 12/2001 |
| EP | 2103268 | 9/2009 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |

OTHER PUBLICATIONS

U.S. Appl. No. 12/176,679, filed Jul. 21, 2008.
U.S. Appl. No. 12/192,170, filed Aug. 15, 2008.
U.S. Appl. No. 12/192,189, filed Aug. 15, 2008.
U.S. Appl. No. 12/192,243, filed Aug. 15, 2008.
U.S. Appl. No. 12/195,624, filed Aug. 21, 2008.
U.S. Appl. No. 12/200,154, filed Aug. 28, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/204,976, filed Sep. 5, 2008.
U.S. Appl. No. 12/210,598, filed Sep. 15, 2008.
U.S. Appl. No. 12/211,205, filed Sep. 16, 2008.
U.S. Appl. No. 12/233,157, filed Sep. 18, 2008.
U.S. Appl. No. 12/236,666, filed Sep. 24, 2008.
U.S. Appl. No. 12/237,515, filed Sep. 25, 2008.
U.S. Appl. No. 12/237,556, filed Sep. 25, 2008.
U.S. Appl. No. 12/237,582, filed Sep. 25, 2008.
U.S. Appl. No. 12/244,873, filed Oct. 3, 2008.
U.S. Appl. No. 12/246,553, filed Oct. 7, 2008.
U.S. Appl. No. 12/248,104, filed Oct. 9, 2008.
U.S. Appl. No. 12/248,115, filed Oct. 9, 2008.
U.S. Appl. No. 12/254,123, filed Oct. 20, 2008.
U.S. Appl. No. 12/331,643, filed Dec. 10, 2008.
U.S. Appl. No. 12/336,970, filed Dec. 17, 2008.
U.S. Appl. No. 12/352,942, filed Jan. 13, 2009.
U.S. Appl. No. 12/353,466, filed Jan. 14, 2009.
U.S. Appl. No. 12/353,470, filed Jan. 14, 2009.
U.S. Appl. No. 12/353,474, filed Jan. 14, 2009.
U.S. Appl. No. 12/363,086, filed Jan. 30, 2009.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/503,256, filed Jul. 15, 2009.
U.S. Appl. No. 12/508,052, filed Jul. 23, 2009.
U.S. Appl. No. 12/535,869, filed Aug. 5, 2009.
U.S. Appl. No. 12/543,831, filed Aug. 19, 2009.
U.S. Appl. No. 12/543,969, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.

(56) References Cited

OTHER PUBLICATIONS

E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing For Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.

(56) References Cited

OTHER PUBLICATIONS

Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 003813.4 dated Aug. 3, 2009.
Int'l Search Report EP 09 004491.8 dated Sep. 9, 2009.
Int'l Search Report EP 09 005575.7 dated Sep. 9, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/13273 dated Dec. 15, 2004.
Int'l Search Report PCT/US04/15311 dated Jan. 12, 2005.
Int'l Search Report PCT/US08/61498 dated Sep. 22, 2008.
Int'l Search Report PCT/US09/032690 dated Jun. 16, 2009.

* cited by examiner

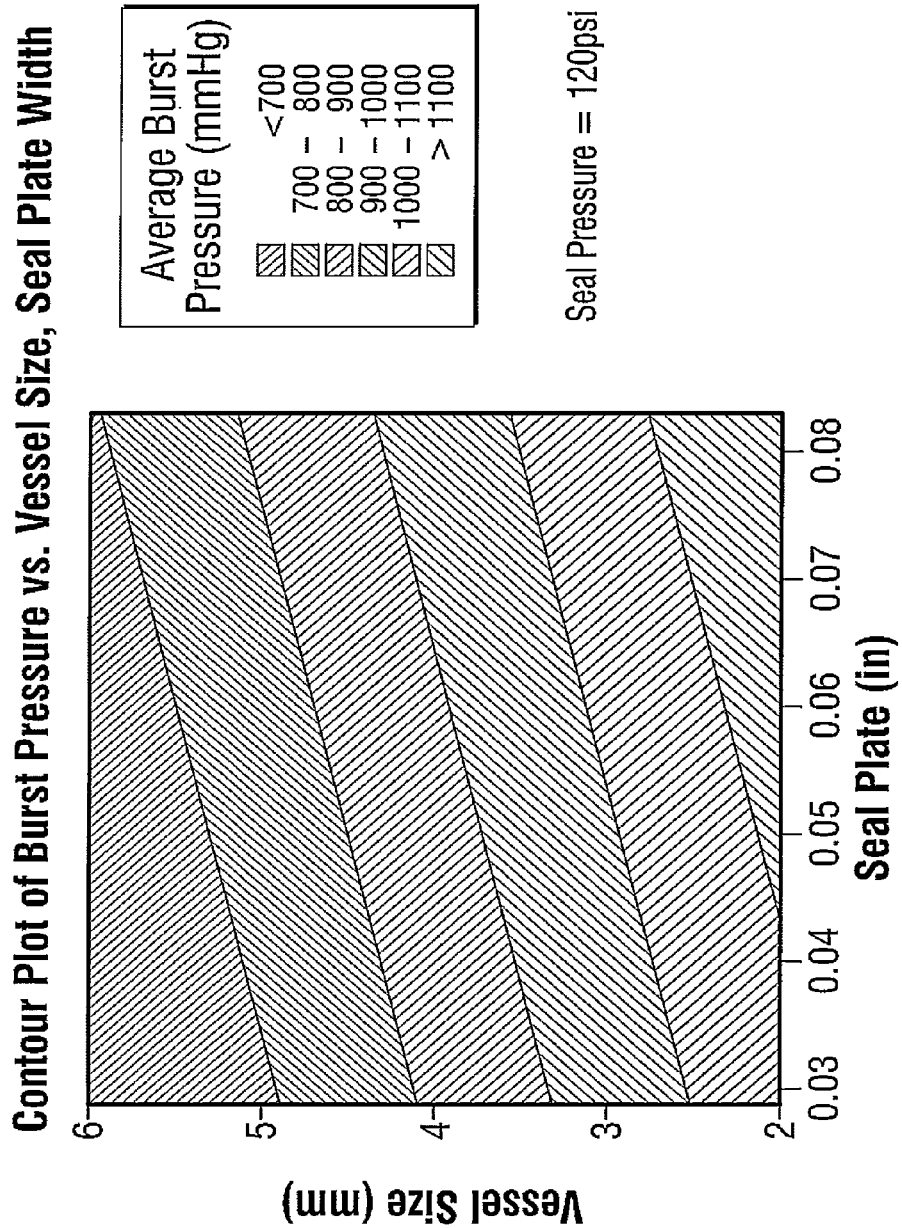

SURGICAL FORCEPS CAPABLE OF ADJUSTING SEAL PLATE WIDTH BASED ON VESSEL SIZE

BACKGROUND

The present disclosure relates to a surgical forceps, and more particularly, to a surgical forceps and method for determining and adjusting a seal plate width based upon a diameter of tissue to be sealed.

TECHNICAL FIELD

As an alternative to open forceps for use with open surgical procedures, modern surgeons use endoscopic or laparoscopic instruments for remotely accessing organs through smaller, puncture-like incisions. More recently, Natural Orifice Translumenal Endoscopic Surgery (NOTES) procedures have been developed, for example, to access the abdominal cavity via the mouth, for scar-less surgery. Much like laparoscopy, NOTES is beneficial to patients in that it reduces scarring and healing time. However, while these minimally invasive surgical procedures are advantageous in many respects, the reduced access area presents new problems for surgical instrument design. For example, achieving a high seal pressure with a surgical forceps becomes increasingly more difficult as the size of the jaw members decrease.

Further, it has been found that the seal pressure required to adequately seal a vessel is dependent on both the vessel size and seal plate width. Accurate application of pressure is important to oppose the walls of the vessel, to reduce tissue impedance to a low enough value that allows enough electrosurgical energy through tissue, to overcome the forces of expansion during tissue heating, and to contribute to the end tissue thickness which is an indication of a good seal. If the pressure is not great enough, the vessel may not properly or effectively seal and if the pressure is too great, the seal may shred or tear.

Accordingly, instead of attempting to identify and apply a specific pressure to a vessel according to vessel size and seal plate width, a pre-determined pressure may be applied to adequately seal different size vessels if the seal plate widths are adjustable according to the diameter of the vessel to be sealed. Such a feature would also be advantageous in the design of surgical instruments in that a designer need not provide an instrument capable of applying a wide-range of seal pressures, but, rather, can provide an instrument capable of applying a single pre-determined pressure for sealing vessels.

SUMMARY

In accordance with the present disclosure, a surgical forceps is provided that includes a housing having a shaft attached to the housing. An end effector assembly is attached at a distal end of the shaft. The end effector assembly includes first and second jaw members having opposed seal plates, each of the seal plates having a width. One or both jaw members are moveable from an open position to a closed position for grasping tissue. A sensing component is configured to determine an output relating to a diameter of tissue and/or a composition of tissue disposed between the opposed seal plates. An expanding component is configured to expand the width of one or both seal plates according to the determined output.

In one embodiment, the sensing component includes a pair of electrodes operably associated with the jaw members. The electrodes are configured to measure an electrical characteristic of tissue disposed between the jaw members, thereby determining the diameter of tissue or the composition of tissue disposed therebetween. In one embodiment, the electrical characteristic is impedance.

In another embodiment, a processing component is included. The processing component is configured to convert the output into a seal plate width according to user-input data. The processing component is in communication with the expanding component such that the expanding component expands the seal plate widths according to the width determined by the processing component.

In yet another embodiment, the expanding component includes a shape memory alloy. The shape memory alloy is configured to expand the widths of the seal plates when heated. The shape memory alloy is further configured to allow the seal plates to return to an un-expanded width when cooled.

In yet another embodiment, the expanding component includes an expandable substrate disposed within each jaw member. A lumen is defined through each of the expandable substrates. The lumens are configured for receiving a fluid therethrough for expanding the expandable substrates. As the expandable substrates expand, the respective seal plate widths are expanded as well.

In still yet another embodiment, the expanding component includes a gear assembly configured to expand the widths of the seal plates.

In yet another embodiment, the expanding component includes an expandable scaffold assembly disposed within each jaw member. Each of the expandable scaffold assemblies is configured such that upon expansion, the widths of the seal plates are also expanded.

In still yet another embodiment, one or more handles is provided for moving the jaw members between the open and closed positions. Further, the handle may be configured such that pulling the handle applies a pre-determined seal pressure to seal tissue disposed between the jaw members.

A method of sealing tissue is also provided in accordance with the present disclosure. The method includes providing a forceps having a pair of jaw members. The jaw members have opposed seal plates and one or both jaw members is moveable relative to the other from an open to a closed position for grasping tissue. The method also includes the steps of determining an output relating to a diameter of tissue and/or a composition of tissue disposed between the jaw members, adjusting a width of the opposed seal plates according to the output, and moving jaw members from the open to the closed position. Moving the jaw members from the open to the closed position applies a seal pressure to seal tissue disposed between the jaw members.

In one embodiment, the widths of the seal plates are adjusted according to the output and user-input data.

In another embodiment, moving the jaw members from the open to the closed position applies a pre-determined seal pressure to seal tissue disposed between the jaw members.

BRIEF DESCRIPTION OF THE DRAWINGS

Various embodiments of the subject instrument are described herein with reference to the drawings wherein:

FIG. 9 is a contour plot of the mean burst pressure as a result of seal plate width and vessel size, with a seal pressure of 120 psi.

DETAILED DESCRIPTION

Figure 1:
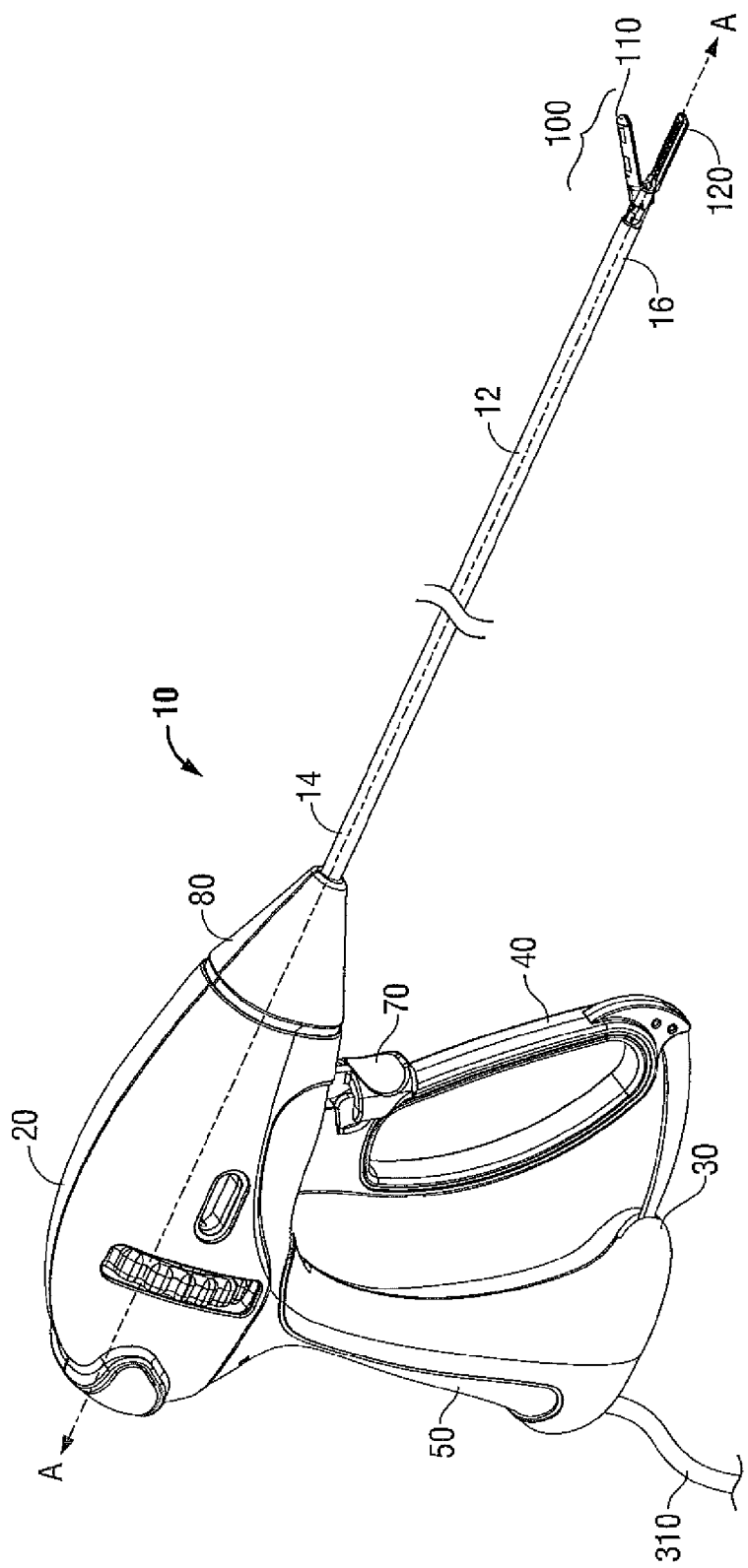
FIG. 1 is a top, perspective view of a surgical forceps including a housing, a handle assembly, a shaft, and an end effector assembly, for use with the present disclosure.

Turning now to FIG. 1, an endoscopic forceps 10 is shown that includes a housing 20, a handle assembly 30, a rotating assembly 80, a trigger assembly 70 and an end effector assembly 100. Forceps 10 further includes a shaft 12 having a proximal end 14 that mechanically engages housing 20 and a distal end 16 configured to mechanically engage end effector assembly 100. Forceps 10 also includes electrosurgical cable 310 that connects forceps 10 to a generator (not shown). Cable 310 has sufficient length to extend through shaft 12 in order to provide electrical energy to at least one of jaw members 110 and 120 of end effector assembly 100.

With continued reference to FIG. 1, rotating assembly 80 is operably coupled to housing 20 and is rotatable approximately 180 degrees in either direction about a longitudinal axis "A" defined through forceps 10. The housing 20 includes two halves that house the internal working components of the forceps 10. Handle assembly 30 includes a moveable handle 40 and a fixed handle 50. Fixed handle 50 is integrally associated with housing 20 and handle 40 is moveable relative to fixed handle 50.

Figure 2:
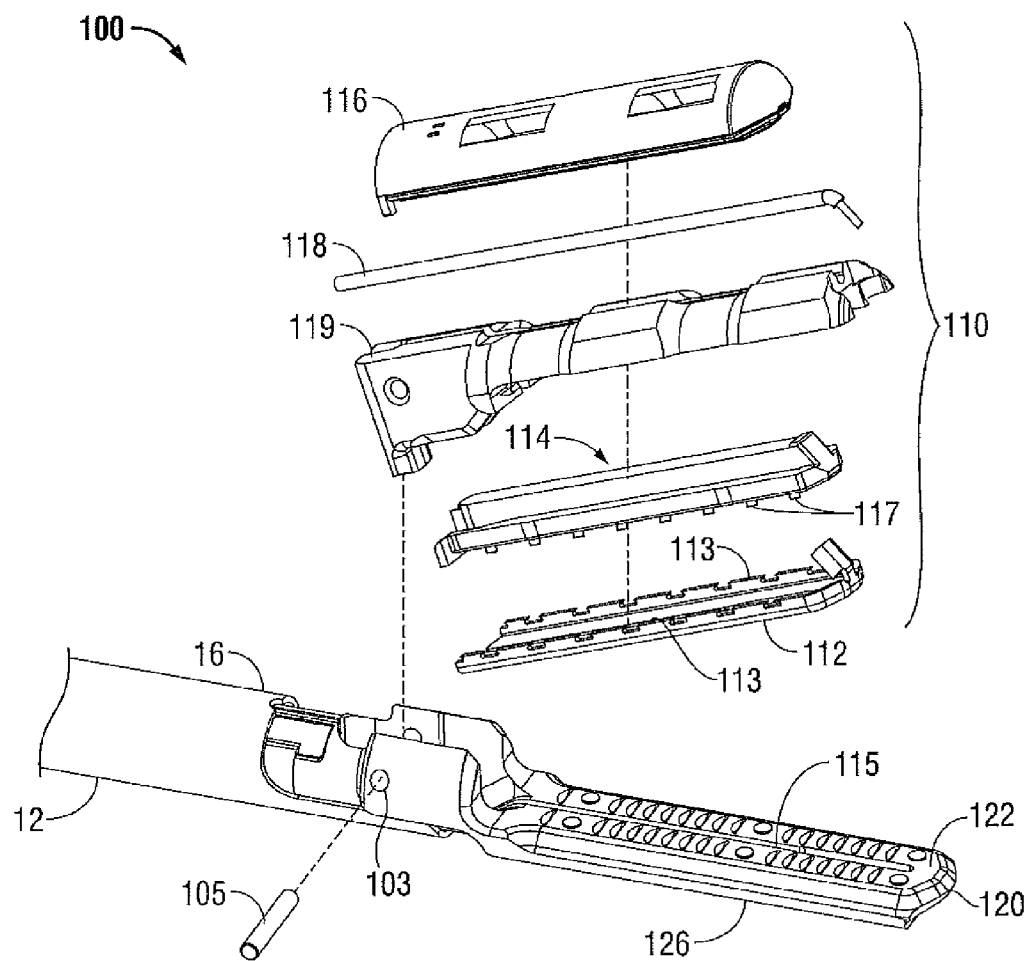
FIG. 2 is a enlarged, side, perspective view of the end effector assembly of FIG. 1 having first and second jaw members, wherein the first jaw is shown with parts separated.

Referring now to FIG. 2, end effector assembly 100 is configured for mechanical attachment at the distal end 16 of shaft 12 of forceps 10. End effector assembly 100 includes opposing jaw members 110 and 120. Handle 40 of forceps 10 (see FIG. 1) ultimately connects to a drive assembly (not shown) which, together, mechanically cooperate to impart movement of the jaw members 110 and 120 from a first, open position wherein the jaw members 110 and 120 are disposed in spaced relation relative to one another, to a second, clamping or closed position wherein the jaw members 110 and 120 cooperate to grasp tissue therebetween. Jaw members 110 and 120 also include longitudinal knife channels 115 defined therein for reciprocation of a knife blade (not shown) therethrough for cutting tissue.

With continued reference to FIG. 2, opposing jaw members 110 and 120 are pivotably connected about pivot 103 via pivot pin 105. Jaw members 110 and 120 include electrically conductive sealing plates 112 and 122, respectively, that are dimensioned to securely engage tissue clamped therebetween. As shown in FIG. 2, seal plate 112 of jaw member 110 includes a number of flanges 113 disposed around a perimeter thereof to engage seal plate 112 with expanding component 114. During assembly, flanges 113 of seal plate 112 are engaged, e.g., slip-fit, with notches 117 of expanding component 114, retaining seal plate 112 thereon. Alternatively, seal plates 112 and 122 may be secured to jaw members 110 and 120, respectively, via any other suitable means. Jaw member 110 further includes a jaw cover 116 for housing the components, e.g., electrodes 118, insulator 119 and expanding component 114, of jaw member 110. Jaw member 120 is constructed similarly to jaw member 110, described above.

As shown in FIG. 2, jaw member 110 includes a sensing component, or electrode pair 118 disposed therethrough. Although not shown in the drawings, jaw member 120 is constructed similarly to jaw member 110 and includes an electrode pair that cooperates with electrode pair 118 to measure the impedance across tissue disposed between the jaw members 110 and 120. Electrode pair 118 of jaw member 110, for example, may be configured to transmit a low-voltage alternating-current through tissue disposed between the jaw members 110 and 120, while the electrode pair disposed through jaw member 120 may be configured to receive the resulting voltage after the voltage has passed through tissue. It is also envisioned that this configuration be reversed, e.g., where the transmitting electrodes are disposed through jaw member 120 and the receiving electrodes are disposed through jaw member 110. In either configuration, the impedance across tissue can be measured and used to determine the diameter of tissue between jaw members 110 and 120.

Alternatively, the impedance across tissue measured by the pairs of electrodes can be used to determine the resistivity of tissue. Since different components of tissue, e.g., muscle cells, fat cells and fluid, have different resistivities, determining the overall resistivity of tissue can help determine the relative composition of tissue. Further, a second pair of electrodes (not shown) or sensors may be disposed through each of the jaw members 110 and 120 such that the first set of electrode pairs may be configured to measure the cross-sectional diameter of tissue while the second set of electrode pairs is configured to measure the resistivity of tissue.

It is also envisioned that any other suitable sensing component may be provided in cooperation with jaw members 110 and 120 to measure the cross-sectional diameter and/or to determine the composition of tissue disposed between jaw members 110 and 120. Further, it is envisioned that the sensing component could include sensors disposed along the sealing plates 112 and 122 of jaw members 110 and 120, respectively, for sensing the gap distance between the respective sealing plates 112 and 122. By determining the gap distance between the sealing plates 112 and 122 at different positions along the plates, the size of the vessel grasped therebetween can be estimated.

Ultimately, the sensing component may be configured to measure any electrical or physical characteristic of tissue that may be used to determine a diameter of tissue or tissue composition. Accordingly, any sensor that may be used to measure an electrical or physical characteristic of tissue may be provided for use with end effector assembly 100 of forceps 10. Suitable sensors include, but are not limited to, impedance sensors, proximity sensors, optical sensors, ultrasonic sensors, chemical sensors, and the like.

Figure 3:
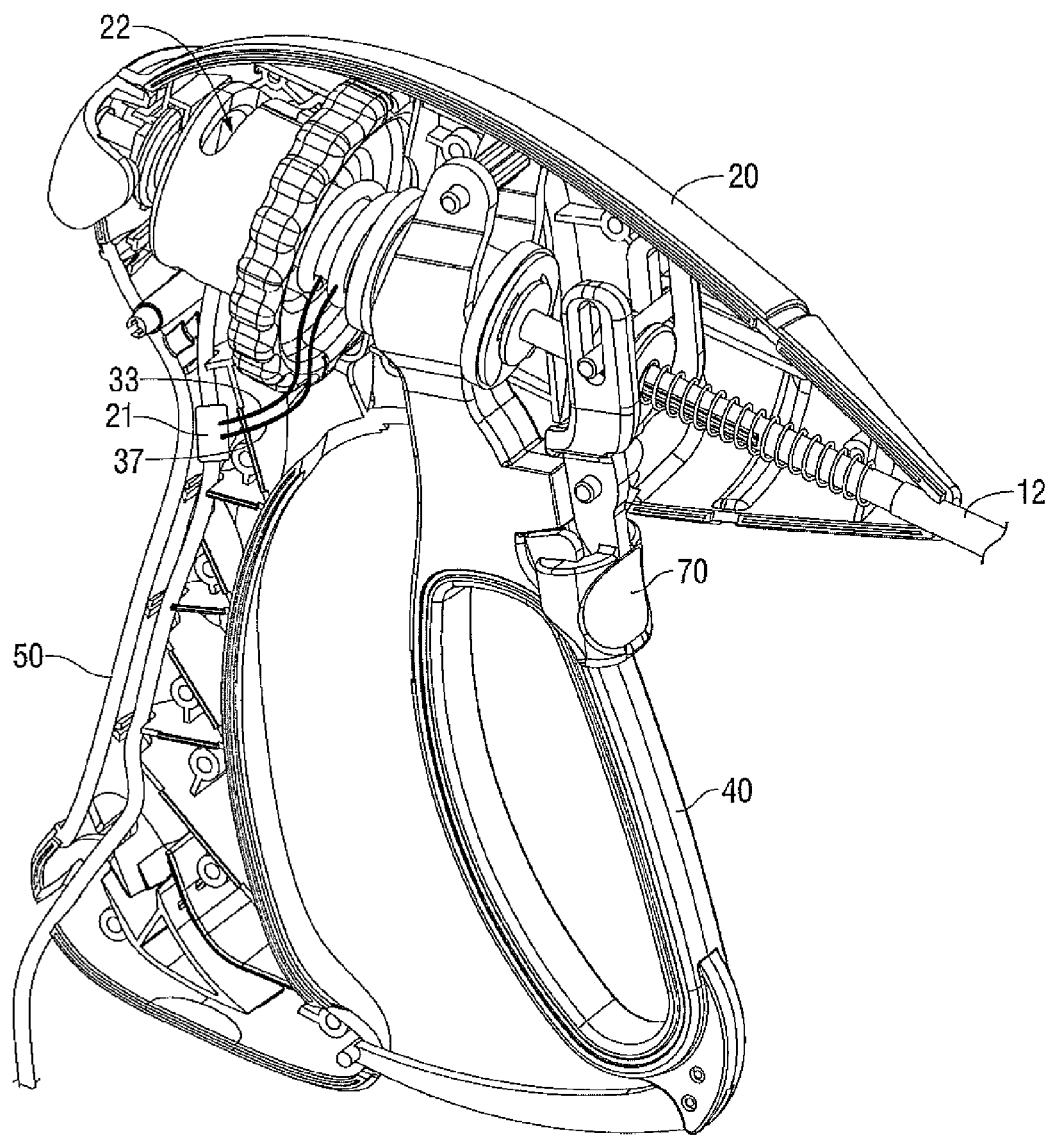
FIG. 3 is a side, perspective view of the housing of the forceps of FIG. 1, with a half of the housing removed.

Referring now to FIG. 3, housing 20 of forceps 10 is shown having a half of housing 20 removed. A processing component 21, disposed within housing 20, is configured to receive the output, e.g., diameter of tissue and/or composition of tissue, from the sensing component 118. One or more leads 33, 37 are disposed through the housing 20 and shaft 12 to the jaw members 110 and 120 to provide feedback to the processing component 21. The processing component 21 converts the output into a seal plate width according to specific characteristics, as determined by the output, of tissue to be sealed.

The processing component 21 may include electrical circuitry 22 configured to convert the output into a seal plate width for adequately sealing tissue disposed between the jaw members 110 and 120. Electrical circuitry 22 may be configured to convert the output to a seal plate width according to specific parameters and/or data. Alternatively, electrical circuitry 22 may communicate with an external source, e.g., a generator (not shown), for determining the seal plate width corresponding to the output. Further, a computer chip (not shown) may be provided for storing data and communicating with the electrical circuitry 22 in order to determine the appropriate seal plate width, based upon the output determined by the sensing component 118. Specific data sets, e.g., the set of seal plate widths required for adequate sealing of vessels having varying diameters, may be used to convert the output into a seal plate width. Algorithms can also be used to determine the seal plate width based upon the specific output determined. Exemplary data, determined by a study of seal plate width as a function of vessel size, for configuring the processing component 21, will be discussed in detail below.

Figure 4:
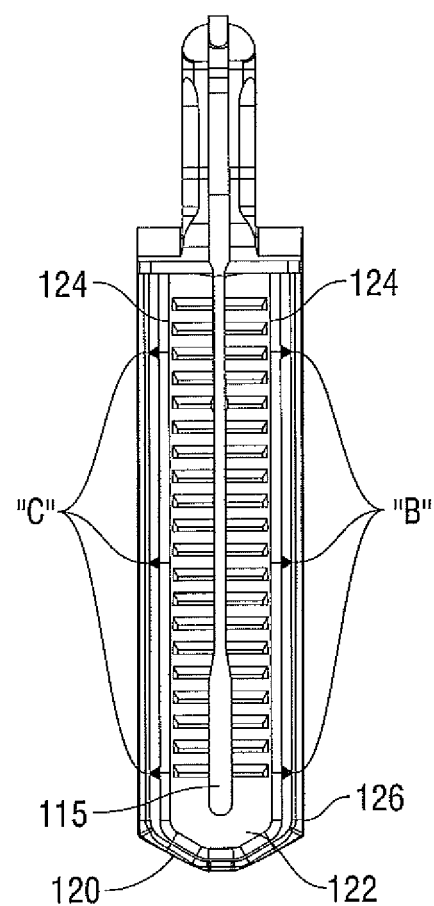
FIG. 4 is a top view of the second jaw member of FIG. 2.

With reference now to FIGS. 2 and 4, once the output has been determined and converted into a seal plate width, e.g., via processing component 21, the specific seal plate width is communicated to the jaw members 110 and 120 such that the expanding component 124 may expand the width of the seal plates 112 and 122 accordingly. In the following, reference will be made to jaw member 120 alone but it is understood that the following relates to both jaw members 110 and 120.

Generally, as shown in FIG. 4, jaw member 120 includes an electrically conductive seal plate 122 and defines longitudinal knife channel 115 therein. As described above, seal plate 122 is engaged with expandable component 124, e.g., with the flanges (not shown, similar to flanges 113 of seal plate 112 (see FIG. 2)) of seal plate 122 slip-fit into notches 127 of expandable component 124, which is contained within jaw cover 126. Expandable component 124 is in communication with processing component 21 of housing 20 (see FIG. 3) such that upon receiving a seal plate width determined by the processing component 21 (as described above), expandable component 124 is expanded to thereby expand seal plate 122 in the direction of arrows "B" and "C," such that the determined width of seal plate 122 is achieved. Accordingly, it is envisioned that seal plate 122 may be configured to have an at-rest width which is a minimum width required to adequately seal tissue. Thus, seal plate 122 need only expand from the seal plate 122 at-rest position to reach the seal plate width required to seal tissue disposed between jaw members 110 and 120.

Various embodiments of the expandable component 124 in conjunction with jaw member 120 will now be described in detail with reference to FIGS. 5A-8B. Jaw member 110 is constructed similarly to jaw member 120 and therefore, to avoid duplication, will not be described herein.

Figure 5A:
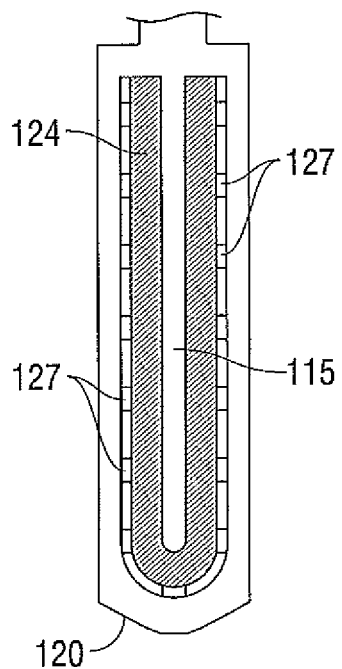
FIGS. 5A-5B show a top view of one embodiment of the second jaw member of FIG. 2 in which a seal plate is removed to show the features thereinbelow.
Figure 5B:
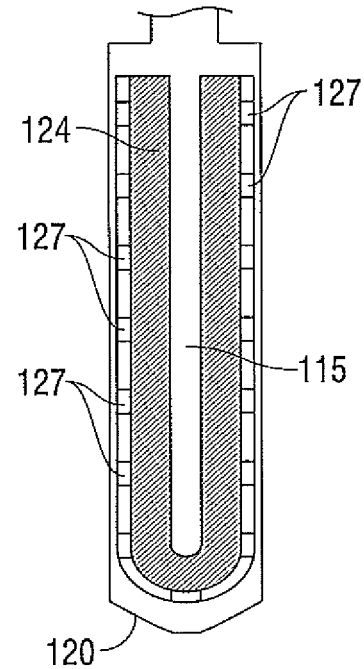

FIGS. 5A-5B show jaw member 120 wherein sealing plate 122 has been removed. As described above, when seal plate 122 is replaced, the flanges (not shown) disposed around the perimeter of seal plate 122 engage notches 127 of expandable component 124, thereby securing seal plate 122 thereon. In the embodiment shown in FIGS. 5A-5B, expandable component 124 is formed at least partially from a shape memory alloy (SMA) 124. The SMA 124 is surrounded by an insulator 124 to prevent heat from passing through to the SMA 124 and to prevent heat from escaping from the SMA 124. SMAs suitable for forming expandable member 124 include, but are not limited to, copper-zinc-aluminum-nickel, copper-aluminum-nickel, and nickel-titanium, commonly referred to in the art as Nitinol alloys. The SMA 124 is configured for two-way shape memory effect. Thus, the SMA 124 associated with sealing plate 122 of jaw member 120 remembers two different shapes, a "cold" shape (e.g., an at-rest position) and a "hot" shape (e.g., an expanded position). For purposes herein, $M_f$ is the temperature at which the transition to a martensite phase or stage is finished during cooling, and $A_s$ and $A_f$ are the temperatures at which the transition from the martensite phase to austenite phase starts and finishes, during heating. $A_s$ may be determined by the SMA material and composition and, typically, ranges from about 150° C. to about 200° C. $A_f$ may also be determined by the SMA material and composition and/or the loading conditions and, typically, ranges from about 2° C. to about 20° C. or hotter.

Expandable member 124 initially may be in an unexpanded position, as shown in FIG. 5A. This unexpanded, or at-rest, position corresponds to the SMA 124 being in a cold state, that is, the SMA is in a martensite state (e.g., $M_f$, a point below $A_s$). When the processing component 21 determines the appropriate seal plate width, a generator (not shown) may be activated to transmit electrosurgical energy through cable 310 into jaw member 120 to heat SMA 124. As SMA 124 "heats up," it eventually reaches an austenite state (e.g., $A_s$) and begins to transition from the "cold" shape to the "hot" shape, which, in turn, causes expandable member 124 to expand. During the austenite phase transition (e.g., $A_s \rightarrow A_f$), the expandable member 124 continues to expand until it reaches a threshold or final austenite stage ($A_f$), shown in FIG. 5B. Since sealing plate 122 is engaged with expanding component 124 via the flanges (not shown) and notches 127, respectively, as the SMA 124 is transitioned (expanded) from the "cold" to the "hot" shape, the width of sealing plate 122 is correspondingly expanded from the unexpanded position of FIG. 5A (corresponding to the "cold" shape of the SMA 124) to the expanded position of FIG. 5B (corresponding to the "hot" shape of the SMA 124). If the SMA 124 is allowed to cool, the SMA 124, as its temperature decreases, will transition from the austenite stage back to the martensite stage such that the SMA 124, and thus the seal plate width, will return to the unexpanded, or at-rest position.

With reference to FIGS. 1-2 and 5A-5B, in operation, as can be appreciated, forceps 10 is positioned such that tissue to be sealed is disposed between jaw member 110 and 120. The sensing components 118 may then be used to determine an output, e.g., the diameter of tissue and/or composition of tissue disposed through jaw members 110 and 120. The determined output is then communicated to the processing component 21 for determining an appropriate seal plate width corresponding to the specific output. Thereafter, an appropriate amount of electrosurgical energy is supplied to expandable member 124, e.g. via a generator (not shown), such that the SMA 124 transitions from its "cold" to its "hot" state, thereby expanding seal plate 122 during this transition. Accordingly, the SMA 124 may be heated to a specific point such that seal plate 122 is expanded to the width determined by the processing component 21. A pre-determined seal pressure may then be applied, e.g., by squeezing handle 40 which, in turn, moves the jaw members 110 and 120 from the open to the closed position, to adequately seal tissue disposed between jaw members 110 and 120.

Figure 6A:
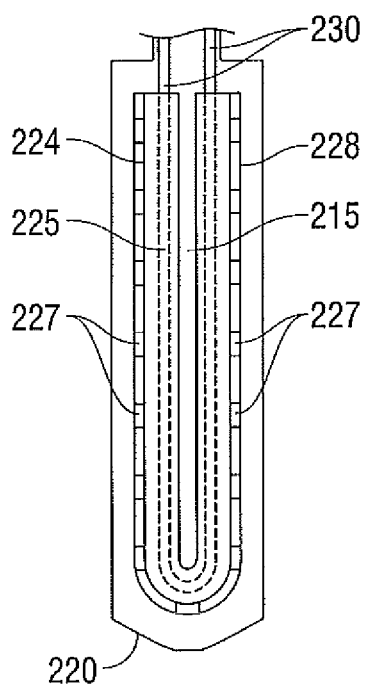
FIGS. 6A-6B show a top view of another embodiment of the second jaw member of FIG. 2 in which the seal plate is removed to show the features thereinbelow.
Figure 6B:
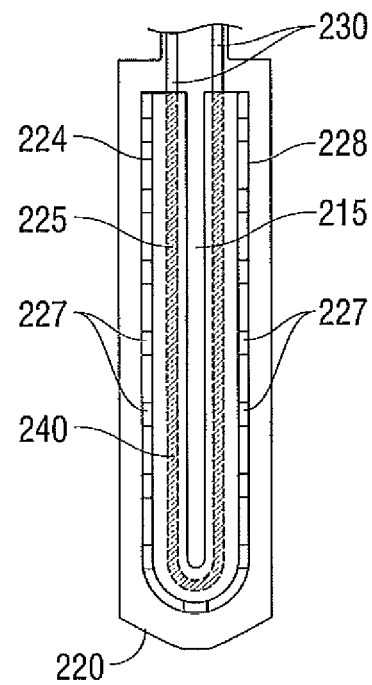

FIGS. 6A-6B illustrate another embodiment of the jaw member 220 wherein the seal plate 122 (FIG. 2) has been removed for viewing purposes. Jaw member 220 includes an expandable substrate 224 defining a "U"-shaped lumen 225 therethrough. Inlet tubes 230 connect lumen 225 of the expandable substrate 224 to an source (not shown) for selectively permitting fluid 240 to flow through lumen 225. A plurality of notches 227 is disposed around the perimeter of expandable substrate 224. Notches 227 are configured to engage the flanges (not shown) of seal plate 122 (FIG. 2) for securing the seal plate 122 (FIG. 2) in place. Knife channel 215 is defined through a central portion of expandable substrate 224.

FIG. 6A shows the expandable substrate in a contracted, or fluid-less state. At this position, expandable substrate 224, and thus seal plate 122 (FIG. 2) have a minimum width. Upon introduction of a fluid 240 through lumen 225 of expandable substrate 224, expandable substrate 224 is expanded to the position shown in FIG. 6B, thereby expanding seal plate 122 (FIG. 2) which is engaged to expandable substrate 224 via the flanges (not shown) and notches 227, respectively. Fluid 240 may be a heated fluid 240, such that, upon passage through lumen 225, fluid 240 heats expandable substrate 224, thereby expanding expandable substrate 224. In this configuration, an insulator 228 is provided to prevent heat transfer between seal plate 122 (FIG. 2) and expandable substrate 224 and vice versa. As can be appreciated, the removal of fluid 240 from lumen 225 allows expandable substrate 224 to cool. As expandable substrate 224 cools, it contracts, thereby contracting the seal plate 122 (FIG. 2). Thus, in operation, fluid 240 may be supplied in varying amounts and/or temperatures to expand the seal plate width according to the determined output.

Figure 7A:
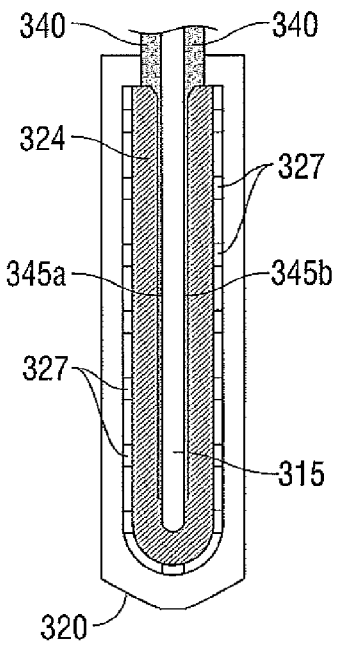
FIGS. 7A-7B show a top view of yet another embodiment of the second jaw member of FIG. 2 in which the seal plate is removed to show the features thereinbelow.
Figure 7B:
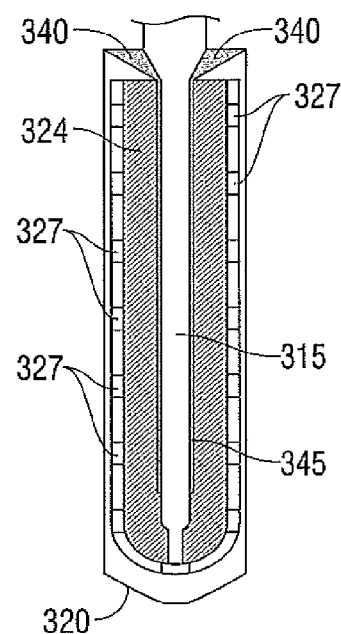

Turning now to the embodiment of FIGS. 7A-7B, jaw member 320 includes expanding component 324 having notches 327 disposed around a perimeter thereof for engagement with the flanges (not shown) of seal plate 122 (FIG. 2). Gear assembly 340 mechanically cooperates with forcing members 345a and 345b to expand and contract expanding component 324. Forcing members 345a and 345b are disposed on either side of knife channel 315 defined within expanding component 324. As shown in FIG. 7A, forcing members 325 are in a contracted, or close, position. Once the sensing component 118 (see FIG. 2) and processing component 21 (see FIG. 3) cooperate to determine the appropriate seal plate width for the particular vessel disposed between jaw members 110 and 120 (FIG. 2), gear assembly 340 is activated to adjust the seal plate width accordingly. For example, gear assembly 340, initially disposed in the position shown in FIG. 7A, may be activated according to the determined diameter of tissue to be sealed such that gear assembly 340 causes forcing members 315 to translate outwardly. Accordingly, expanding component 324, seal plate 122 (FIG. 2), and knife channel 315 are all expanded to the positions shown in FIG. 7B. The position shown in FIG. 7B may correspond to a specific seal plate width according to the specific output determined.

Figure 8A:
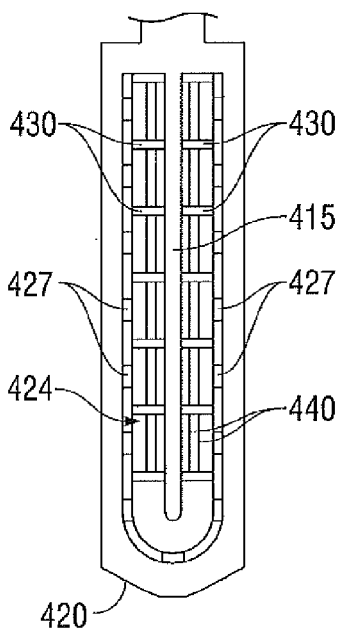
FIGS. 8A-8B show a top view of still yet another embodiment of the second jaw member of FIG. 2 in which the seal plate is removed to show the features thereinbelow.
Figure 8B:
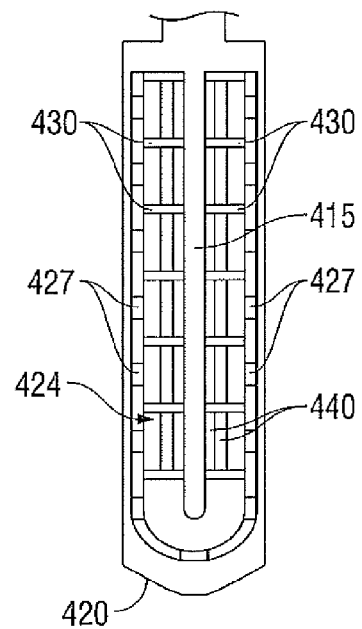

With reference to FIGS. 8A-8B, jaw member 420 is shown having a scaffold assembly 424 disposed thereon. A plurality of notches 427, disposed around the perimeter of scaffold assembly 424, is configured to engage the flanges (not shown) 123 of seal plate 122 (FIG. 2) for securing the seal plate 122 (FIG. 2) thereon. Knife channel 415 is defined through a central portion of scaffold assembly 424. Scaffold assembly 424 includes expanding members 430 and longitudinal bars 440. Longitudinal bars 440 are configured to maintain the integrity of scaffold assembly 424, while expanding members 430 are configured to expand scaffold assembly 424 from the position shown in FIG. 8A to the position shown in FIG. 8B.

In operation, when the determined seal plate width for sealing the particular size tissue disposed between the jaw member requires the current seal plate width to be expanded, expanding members 430 are expanded, thereby forcing longitudinal bars 440 into a spaced-apart configuration with respect to one another. This expansion of scaffold assembly 424 similarly causes the expansion of seal plate 122 (FIG. 2) according to the seal plate width desired. When it is determined that the seal plate width needs to be reduced, expanding members 430 are retracted, bringing longitudinal bars 440 into a closer-together position, thereby retracting scaffold assembly 424 and seal plate 122 (FIG. 2).

Referring to FIGS. 1-3, the above-described embodiments of the jaw members 110 and 120 allow the seal plate width to be adjusted according to the diameter of tissue and/or composition of tissue to be sealed. Adjusting seal plate width allows a user to apply a pre-determined seal pressure to vessels of varying sizes. Thus, a user will not have to apply an estimated seal pressure, e.g., by selectively squeezing handle 40 to an estimated position according to the estimated seal pressure desired. Instead, a user may apply a single, pre-determined seal pressure for a range of vessel sizes. Similarly, the instrument may be designed for application of a single, pre-determined seal pressure, e.g., where the user squeezes handle 40 through its complete range of motion to achieve the pre-determined seal pressure. In either of the above configurations, adequate and effective seals are ensured because two factors affecting the quality of a seal, i.e., vessel size and seal pressure, are used to determine the appropriate seal plate width for sealing tissue according to the above-mentioned factors.

Additionally, seal plates 112 and 122 may be expandable to different widths. As can be appreciated, it may be desirable for seal plates 112 and 122 to be expandable to different widths in order to properly seal tissue according to the specific size, shape, composition, and/or other characteristics of tissue to be sealed. Expanding the opposing seal plates 112, 122 to different widths can be achieved, for example, by allowing the processing component 21 to independently expand the seal plates 112, 122. In such an embodiment, the processing component 21, based upon the determined output, or user input data, would activate the expanding components 114, 124 to independently expand each respective seal plate 112, 122 to a specific width. Thus, if the determined output indicates that seal plates having different widths would be desirable to seal the particular tissue disposed between jaw members 110 and 120, seal plate 112 would be expanded to a first width, while seal plate 122 would be expanded to a second, different width. On the other hand, if it is determined that seal plates having the same width would be more desirable, seal plates 112 and 122 would both be expanded to the specific width determined. Alternatively, only one of the seal plates 112, 122 may be expandable. For example, seal plate 112 may be fixed in position, while seal plate 122 is expandable. In this configuration, seal plate 122 can be expanded to the width of seal plate 112 such that the seal plates 112 and 122 have equal widths, or seal plate 122 may be expanded such that the seal plates 112 and 122 have different widths.

As mentioned above, specific data or formulae may be input into the processing component 21 to determine the appropriate seal plate width corresponding to the diameter of the vessel to be sealed and the seal pressure to be applied. Accordingly, a study was conducted to determine how seal plate width and blood vessel size, under a constant seal pressure, influence the quality of the seal produced, measured through burst pressure. Burst pressure is the pressure required to open, or burst, a previously sealed vessel by forcing a fluid through the sealed vessel. The range of values tested for seal plate width was about 0.03 inches to about 0.08 inches. Vessel diameters ranged from about 2 mm to about 6 mm. In the study discussed above, the vessels were sealed by applying a constant seal pressure of 120 psi. FIG. 9, a contour plot of burst pressure vs. vessel size, shows the results of the study. Data extrapolated from FIG. 9 and/or algorithms corresponding to the results shown in FIG. 9 can be input into processing component 21 for determining the appropriate seal plate width as a function of vessel size (with a constant seal pressure).

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical forceps, the forceps comprising:
   a housing having a shaft attached thereto and an end effector assembly disposed at a distal end thereof, the end effector assembly including:
      first and second jaw members having opposed seal plates, each having a width, at least one jaw member moveable from an open position to a closed position for grasping tissue therebetween, the jaw members configured to apply a pre-determined seal pressure to tissue grasped therebetween;
      a sensing component configured to determine an output relating to a diameter of tissue or a composition of tissue disposed between the opposed seal plates of the first and second jaw members; and
      an expanding component configured to expand the width of at least one of the opposed seal plates according to the determined output and the pre-determined seal pressure.

2. The surgical forceps according to claim 1, wherein the sensing component includes a pair of electrodes operably associated with the jaw members, the electrodes configured to measure at least one electrical characteristic of tissue disposed between the jaw members, to thereby determine the cross-sectional diameter of tissue or the composition of tissue disposed therebetween.

3. The surgical forceps according to claim 2, wherein the electrical characteristic is impedance.

4. The forceps according to claim 1 further comprising a processing component configured to convert the determined output into a seal plate width, the processing component further configured to communicate with the expanding component for expanding the seal plate width according to the seal plate width.

5. The forceps according to claim 1, wherein the expanding component includes a shape memory alloy, the shape memory alloy configured to expand the width of the at least one of the seal plates when heated and configured to allow the at least one of the seal plates to return to an un-expanded width when cooled.

6. The forceps according to claim 1, wherein the expanding component includes an expandable substrate disposed within each jaw member, each expandable substrate defining a lumen therethrough and configured for introduction of a fluid therein to expand the expandable substrate, to thereby expand the width of the at least one of the seal plates.

7. The forceps according to claim 1, wherein the expanding component includes a gear assembly configured to expand a portion of at least one of the jaw members to expand the width of the at least one of the seal plates.

8. The forceps according to claim 1, further comprising at least one handle operably coupled to at least one of the jaw members, the at least one handle configured to move between a first position and a second position to move the jaw members between the open and closed positions.

9. The forceps according to claim 8, wherein, in the second position of the at least one handle, the jaw members are configured to apply the pre-determined seal pressure to tissue disposed between the jaw members.

10. A method of sealing tissue, the method comprising the steps of:
    providing a forceps including a pair of jaw members having opposed seal plates, at least one jaw member moveable relative to the other from an open to a closed position for grasping tissue therebetween and to apply a pre-determined seal pressure to tissue grasped therebetween;
    determining an output relative to a diameter of tissue or a composition of tissue disposed between the jaw members;
    adjusting a width of at least one of the opposed seal plates according to the determined output and the pre-determined seal pressure; and
    moving the at least one jaw member from the open to the closed position to apply the pre-determined seal pressure to seal tissue disposed between the jaw members.

11. The method according to claim 10, wherein the width of the at least one seal plate is adjusted according to the output and user-input data.

* * * * *